(12) United States Patent
Cook et al.

(10) Patent No.: US 12,144,686 B2
(45) Date of Patent: Nov. 19, 2024

(54) AUTOMATIC DEPTH SELECTION FOR ULTRASOUND IMAGING

(71) Applicant: EchoNous, Inc., Redmond, WA (US)

(72) Inventors: Matthew Cook, Woodinville, WA (US); Babajide Ayinde, Redmond, WA (US)

(73) Assignee: Echonous, Inc., Redmond, WA (US)

( * ) Notice: Subject to any disclaimer, the term of this patent is extended or adjusted under 35 U.S.C. 154(b) by 0 days.

(21) Appl. No.: 17/509,987

(22) Filed: Oct. 25, 2021

(65) Prior Publication Data

US 2023/0125779 A1    Apr. 27, 2023

(51) Int. Cl.
*A61B 8/08* (2006.01)
*A61B 8/00* (2006.01)
*G06N 3/08* (2023.01)

(52) U.S. Cl.
CPC .......... *A61B 8/5207* (2013.01); *A61B 8/0883* (2013.01); *A61B 8/4427* (2013.01); *A61B 8/54* (2013.01); *G06N 3/08* (2013.01)

(58) Field of Classification Search
CPC .................................................. A61B 8/0883
See application file for complete search history.

(56) References Cited

U.S. PATENT DOCUMENTS

| | | | |
|---|---|---|---|
| 10,430,946 B1 | 10/2019 | Zhou et al. | |
| 10,631,828 B1 * | 4/2020 | Hare, II | G16H 30/20 |
| 11,308,609 B2 * | 4/2022 | Annangi | A61B 8/54 |
| 2017/0143312 A1 * | 5/2017 | Hedlund | A61B 6/487 |
| 2017/0360403 A1 | 12/2017 | Rothberg et al. | |
| 2018/0259608 A1 | 9/2018 | Golden et al. | |
| 2019/0105019 A1 * | 4/2019 | Pagoulatos | A61B 5/333 |
| 2019/0125298 A1 * | 5/2019 | Abolmaesumi | A61B 8/4405 |
| 2019/0140596 A1 | 5/2019 | Shimamoto et al. | |
| 2019/0307428 A1 * | 10/2019 | Silberman | A61B 8/467 |
| 2020/0054306 A1 | 2/2020 | Mehanian et al. | |
| 2020/0260062 A1 | 8/2020 | Sharma et al. | |
| 2021/0068791 A1 * | 3/2021 | Gebre | G16H 50/20 |
| 2021/0137416 A1 * | 5/2021 | Canfield | G16H 50/30 |

(Continued)

FOREIGN PATENT DOCUMENTS

| | | |
|---|---|---|
| CN | 108079446 A | 5/2018 |
| CN | 112754518 A | 5/2021 |

(Continued)

OTHER PUBLICATIONS

Gal, Y., et al., "Dropout as a Bayesian Approximation: Representing Model Uncertainty in Deep Learning," Proceedings of the 33rd International Conference on Machine Learning, New York, NY, 2016, retrieved from arXiv:1506.02142v6, 12 pages.

(Continued)

*Primary Examiner* — Joel Lamprecht
*Assistant Examiner* — Nyrobi Celestine
(74) *Attorney, Agent, or Firm* — Seed Intellectual Property Law Group LLP

(57) ABSTRACT

A facility for assessing an ultrasound image captured from a patient with a particular depth setting is described. The facility subjects the received ultrasound image to at least one neural network to produce, for each neural network, an inference. On the basis of the produced inferences, the facility determines whether the depth setting at which the ultrasound image was captured was optimal.

16 Claims, 12 Drawing Sheets

(56) References Cited

U.S. PATENT DOCUMENTS

| | | | |
|---|---|---|---|
| 2021/0177373 A1* | 6/2021 | Xie | G06N 3/04 |
| 2021/0345992 A1 | 11/2021 | Cook et al. | |
| 2021/0350529 A1 | 11/2021 | Ayinde et al. | |

FOREIGN PATENT DOCUMENTS

| | | | |
|---|---|---|---|
| EP | 3536245 | A1 | 9/2019 |
| KR | 102245150 | B1 | 4/2021 |
| WO | 2018026431 | A1 | 2/2018 |
| WO | 2018140596 | A2 | 8/2018 |
| WO | 2019201726 | A1 | 10/2019 |
| WO | 2020/020770 | A1 | 1/2020 |
| WO | 2020020809 | A1 | 1/2020 |
| WO | 2020/216753 | A1 | 10/2020 |

OTHER PUBLICATIONS

Geifman, Y., et al., "Selective Classification for Deep Neural Networks," Jun. 2, 2017, retrieved from arXiv:1705.08500v2, 12 pages.

Lakshminarayanan, B., et al., "Simple and Scalable Predictive Uncertainty Estimation Using Deep Ensembles," 31st Conference on Neural Information Processing Systems (NIPS 2017), Long Beach, CA, retrieved from arXiv:1612.01474v3, 15 pages.

Liu, S. et al., "Deep learning in Medical Ultrasound Analysis: A Review," (2019). Engineering, 5(2): 261-275.

International Search Report and Written Opinion, dated Aug. 25, 2021, for International Application No. PCT/US2021/031415, 10 pages.

American Institute of Ultrasound in Medicine, "AIUM Practice Guideline for the Performance of the Focused Assessment With Sonography for Trauma (FAST) Examination," *J Ultrasound Med* 33:2047-2056, 2014.

International Search Report and Written Opinion, dated Oct. 12, 2021, for International Application No. PCT/US2021/031193, 9 pages.

Redmon et al., "YOLOv3: An Incremental Improvement," Apr. 8, 2018, retrieved from arxiv.org/abs/1804.02767, 6 pages.

International Search Report and Written Opinion, dated Feb. 24, 2022, for International Application No. PCT/US2021/058037. (11 pages).

International Search Report and Written Opinion of the International Search Authority, mailed Mar. 2, 2023, for International Application No. PCT/US2022/047320, 12 pages.

\* cited by examiner

| View | Object Name | Average Optimal Margin (cm) |
|---|---|---|
| Apical-2-Chamber | Left Atrium | 3.4 |
| Apical-2-Chamber | Left Ventricle | 8.11 |
| Apical-2-Chamber | Mitral Valve | 6.74 |
| Apical-4-Chamber | Left Atrium | 4.61 |
| Apical-4-Chamber | Left Ventricle | 8.88 |
| Apical-4-Chamber | Mitral Valve | 7.38 |
| Parasternal Long Axis | Left Atrium | 4.99 |
| Parasternal Long Axis | Left Ventricle | 6.48 |
| Parasternal Long Axis | Mitral Valve | 5.22 |
| ... | ... | ... |

*FIG. 6*

AUTOMATIC DEPTH SELECTION FOR ULTRASOUND IMAGING

BACKGROUND

Ultrasound imaging is a useful medical imaging modality. For example, internal structures of a patient's body may be imaged before, during or after a therapeutic intervention. A healthcare professional typically holds a portable ultrasound probe, sometimes called a "transducer," in proximity to the patient and moves the transducer as appropriate to visualize one or more target structures in a region of interest in the patient. A transducer may be placed on the surface of the body or, in some procedures, a transducer is inserted inside the patient's body. The healthcare professional coordinates the movement of the transducer so as to obtain a desired representation on a screen, such as a two-dimensional cross-section of a three-dimensional volume.

Particular views of an organ or other tissue or body feature (such as fluids, bones, joints or the like) can be clinically significant. Such views may be prescribed by clinical standards as views that should be captured by the ultrasound operator, depending on the target organ, diagnostic purpose or the like.

The view of the interior of the patient's body in an ultrasound image typically extends downward from the active surface of the transducer to a certain "depth"—i.e., a certain distance below the transducer's active surface. This depth is among a number of settings of the ultrasound device that can be adjusted by the sonographer or other person using the ultrasound device in order to optimize the produced images for their intended purpose. For example, the operator would generally select a depth large enough to entirely capture the region of interest, but not so large as to extend much beyond (below) the region of interest.

The operator typically manually selects the depth using a particular control integrated into the ultrasound device, such as a knob or a pair of buttons. It is common for an experienced operator to progressively select different depth values, observing the resulting images and continuing to adjust the depth until a depth is found that is effective in capturing all of the region of interest, but not much deeper.

BRIEF DESCRIPTION OF THE DRAWINGS

FIG. 6 is a table diagram showing sample contents of an optimal margin table constructed and/or used by the facility in some embodiments.

DETAILED DESCRIPTION

Figure 1:
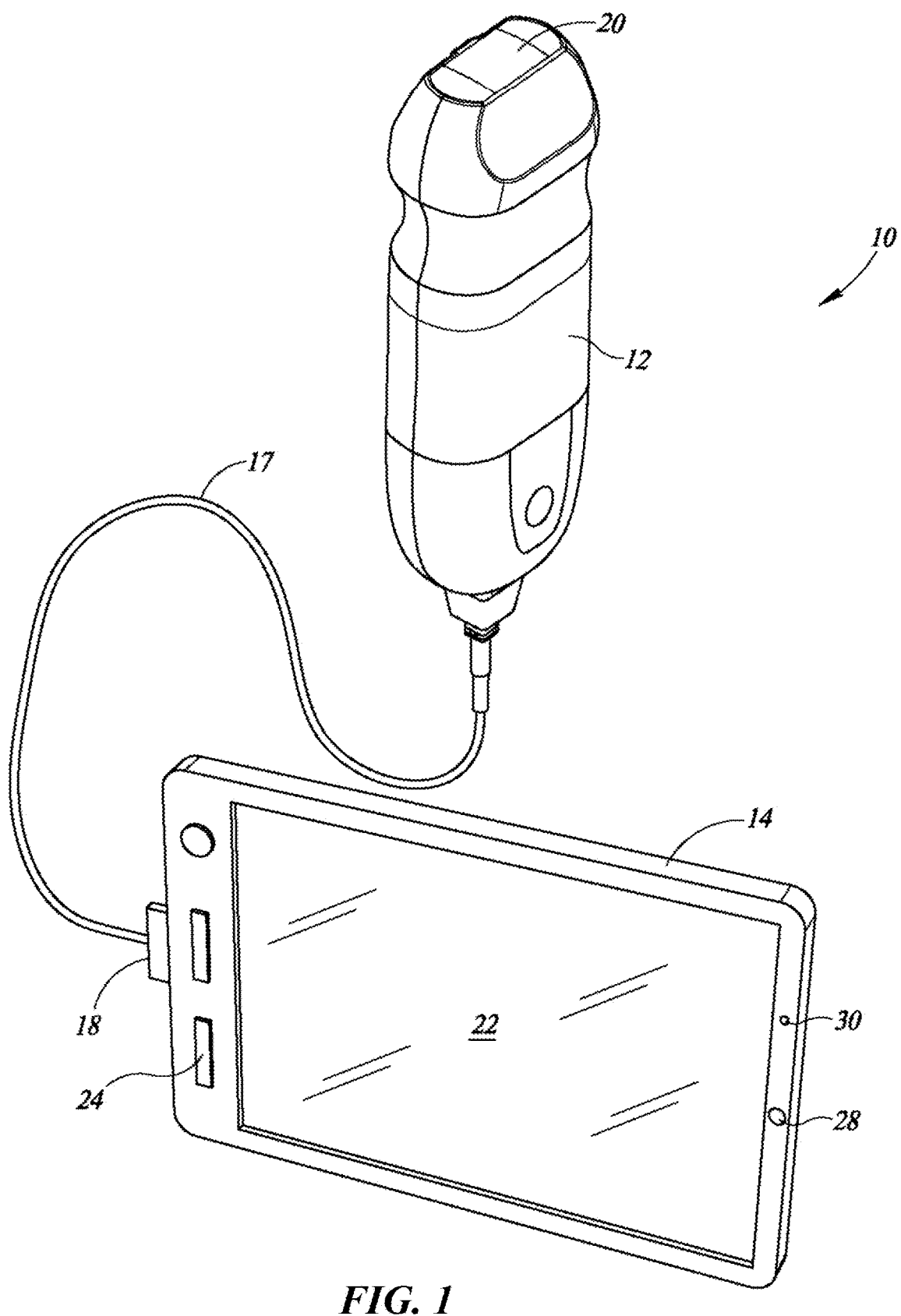
FIG. 1 is a schematic illustration of a physiological sensing device 10, in accordance with one or more embodiments of the present disclosure.

The inventors have recognized that conventional approaches to controlling the depth setting of an ultrasound device have significant disadvantages. In particular, the conventional approaches require manual input from the operator. This adds to the difficulty of the operator's image capture task, particularly making it less likely that the task will be performed effectively via a novice operator; has associated with it a certain level of error, frequently degrading the value of the produced images for their intended purpose; and extends the amount of time it takes to perform each ultrasound study. In particular, where the depth is too small, this interferes with the ability to view and assess the entire region of interest, such as an entire sub-organ anatomical structure, like the left ventricle; where the depth is too great, the entire region of interest is visible, but at a lower resolution than would be optimal for viewing and assessing it.

In response to recognizing these disadvantages, the inventors have conceived and reduced to practice a software and/or hardware facility that uses machine learning to automatically select a depth for ultrasound imaging ("the facility").

In some embodiments, the facility trains and applies a direct, qualitative machine learning model. The direct machine learning model uses an artificial neural network to predict, for an ultrasound image captured with a particular depth setting: (1) the probability that the depth setting was too small—i.e., the entire region of interest was not captured, or the region of interest was captured with an inadequate margin beneath it; (2) the probability that the depth setting was optimal or nearly optimal; and (3) the probability that the depth setting was too large—i.e., the entire region of interest was captured with a margin beneath it that is too large. In some such embodiments, for images where the predicted probability that the depth setting is too small is higher than the other two probabilities, the facility automatically controls the ultrasound device to capture another image at a higher depth setting, or prompts the device's operator to do this. For images where the predicted probability that the depth setting is too large is higher than the other two probabilities, the facility automatically controls the ultrasound device to capture another image at a lower depth setting, or prompts the device's operator to do this.

In some embodiments, the facility trains and applies an indirect, view-based, quantitative machine learning model that predicts, for an ultrasound image captured with a particular depth setting, the direction and magnitude by which the depth setting must be changed to be optimal. In this model, one or more neural networks predict: (1) a view to which the image corresponds (A view is an approach to capturing a particular region of interest from a particular perspective); and (2) localization of objects within the image, such as via object detection and/or object segmentation. Localization results include both object type and object location in the image. For each identified object, the facility: (1) calculates the distance from the bottom of the object to the bottom of the image; (2) uses the predicted view plus the identified object to retrieve an empirically-determined optimal distance from the bottom of the object to the bottom of the image, and (3) subtracts the calculated distance from the retrieved distance to obtain a signed recommended change in the depth setting. Where multiple objects are identified, the facility aggregates these recommended changes across the objects, such as by determining their median. In some embodiments, the facility automatically controls the ultrasound device to capture another image at a new depth to which the signed recommended change has been added, or prompts the device's operator to do this.

In some embodiments, the facility applies both models to each image, and only automatically changes the depth setting or prompts the operator to do this where the results produced for the image by both models agree.

In various embodiments, the facility is adapted to different imaging sites, including the heart (cardiac ultrasound), the liver, the kidneys, pleural line or rib spaces in or near the lungs, or veins or nerves in musculoskeletal ultrasound, as examples. In various embodiments, the facility is adapted to various imaging modalities, including computed tomography, magnetic resonance imaging, mammogram, fluoroscopy, and positron-emission tomography.

By performing in some or all of these ways, the facility produces more suitable ultrasound images in a shorter period of time, without relying on the ability of the ultrasound device's operator to manually select appropriate depth settings. This makes less experienced operators of the device more successful and more confident in using the device.

Additionally, the facility improves the functioning of computer or other hardware, such as by reducing the dynamic display area, processing, storage, and/or data transmission resources needed to perform a certain task, thereby enabling the task to be permitted by less capable, capacious, and/or expensive hardware devices, and/or be performed with lesser latency, and/or preserving more of the conserved resources for use in performing other tasks. For example, by shortening the average length in time of an ultrasound session, a clinic or other medical facility in which ultrasound devices are used can reduce the total cost of purchasing and maintaining ultrasound devices by purchasing and using fewer devices to perform the same volume of studies. Alternatively, the clinic can perform a greater volume of studies with the same number of ultrasound devices.

FIG. 1 is a schematic illustration of a physiological sensing device 10, in accordance with one or more embodiments of the present disclosure. The device 10 includes a probe 12 that, in the illustrated embodiment, is electrically coupled to a handheld computing device 14 by a cable 17. The cable 17 includes a connector 18 that detachably connects the probe 12 to the computing device 14. The handheld computing device 14 may be any portable computing device having a display, such as a tablet computer, a smartphone, or the like. In some embodiments, the probe 12 need not be electrically coupled to the handheld computing device 14, but may operate independently of the handheld computing device 14, and the probe 12 may communicate with the handheld computing device 14 via a wireless communication channel.

The probe 12 is configured to transmit an ultrasound signal toward a target structure and to receive echo signals returning from the target structure in response to transmission of the ultrasound signal. The probe 12 includes an ultrasound sensor 20 that, in various embodiments, may include an array of transducer elements (e.g., a transducer array) capable of transmitting an ultrasound signal and receiving subsequent echo signals.

The device 10 further includes processing circuitry and driving circuitry. In part, the processing circuitry controls the transmission of the ultrasound signal from the ultrasound sensor 20. The driving circuitry is operatively coupled to the ultrasound sensor 20 for driving the transmission of the ultrasound signal, e.g., in response to a control signal received from the processing circuitry. The driving circuitry and processor circuitry may be included in one or both of the probe 12 and the handheld computing device 14. The device 10 also includes a power supply that provides power to the driving circuitry for transmission of the ultrasound signal, for example, in a pulsed wave or a continuous wave mode of operation.

The ultrasound sensor 20 of the probe 12 may include one or more transmit transducer elements that transmit the ultrasound signal and one or more receive transducer elements that receive echo signals returning from a target structure in response to transmission of the ultrasound signal. In some embodiments, some or all of the transducer elements of the ultrasound sensor 20 may act as transmit transducer elements during a first period of time and as receive transducer elements during a second period of time that is different than the first period of time (i.e., the same transducer elements may be usable to transmit the ultrasound signal and to receive echo signals at different times).

The computing device 14 shown in FIG. 1 includes a display screen 22 and a user interface 24. The display screen 22 may be a display incorporating any type of display technology including, but not limited to, LCD or LED display technology. The display screen 22 is used to display one or more images generated from echo data obtained from the echo signals received in response to transmission of an ultrasound signal, and in some embodiments, the display screen 22 may be used to display color flow image information, for example, as may be provided in a Color Doppler imaging (CDI) mode. Moreover, in some embodiments, the display screen 22 may be used to display audio waveforms, such as waveforms representative of an acquired or conditioned auscultation signal.

In some embodiments, the display screen 22 may be a touch screen capable of receiving input from an operator that touches the screen. In such embodiments, the user interface 24 may include a portion or the entire display screen 22, which is capable of receiving operator input via touch. In some embodiments, the user interface 24 may include one or more buttons, knobs, switches, and the like, capable of receiving input from an operator of the ultrasound device 10. In some embodiments, the user interface 24 may include a microphone 30 capable of receiving audible input, such as voice commands.

The computing device 14 may further include one or more audio speakers 28 that may be used to output acquired or conditioned auscultation signals, or audible representations of echo signals, blood flow during Doppler ultrasound imaging, or other features derived from operation of the device 10.

The probe 12 includes a housing, which forms an external portion of the probe 12. The housing includes a sensor portion located near a distal end of the housing, and a handle portion located between a proximal end and the distal end of the housing. The handle portion is proximally located with respect to the sensor portion.

The handle portion is a portion of the housing that is gripped by an operator to hold, control, and manipulate the probe 12 during use. The handle portion may include gripping features, such as one or more detents, and in some embodiments, the handle portion may have a same general shape as portions of the housing that are distal to, or proximal to, the handle portion.

The housing surrounds internal electronic components and/or circuitry of the probe 12, including, for example, electronics such as driving circuitry, processing circuitry, oscillators, beamforming circuitry, filtering circuitry, and the like. The housing may be formed to surround or at least partially surround externally located portions of the probe 12, such as a sensing surface. The housing may be a sealed housing, such that moisture, liquid or other fluids are prevented from entering the housing. The housing may be formed of any suitable materials, and in some embodiments, the housing is formed of a plastic material. The housing may be formed of a single piece (e.g., a single material that is molded surrounding the internal components) or may be formed of two or more pieces (e.g., upper and lower halves) which are bonded or otherwise attached to one another.

In some embodiments, the probe 12 includes a motion sensor. The motion sensor is operable to sense a motion of the probe 12. The motion sensor is included in or on the probe 12 and may include, for example, one or more accelerometers, magnetometers, or gyroscopes for sensing motion of the probe 12. For example, the motion sensor may be or include any of a piezoelectric, piezoresistive, or capacitive accelerometer capable of sensing motion of the probe 12. In some embodiments, the motion sensor is a tri-axial motion sensor capable of sensing motion about any of three axes. In some embodiments, more than one motion sensor 16 is included in or on the probe 12. In some embodiments, the motion sensor includes at least one accelerometer and at least one gyroscope.

The motion sensor may be housed at least partially within the housing of the probe 12. In some embodiments, the motion sensor is positioned at or near the sensing surface of the probe 12. In some embodiments, the sensing surface is a surface which is operably brought into contact with a patient during an examination, such as for ultrasound imaging or auscultation sensing. The ultrasound sensor 20 and one or more auscultation sensors are positioned on, at, or near the sensing surface.

In some embodiments, the transducer array of the ultrasound sensor 20 is a one-dimensional (1D) array or a two-dimensional (2D) array of transducer elements. The transducer array may include piezoelectric ceramics, such as lead zirconate titanate (PZT), or may be based on microelectromechanical systems (MEMS). For example, in various embodiments, the ultrasound sensor 20 may include piezoelectric micromachined ultrasonic transducers (PMUT), which are microelectromechanical systems (MEMS)-based piezoelectric ultrasonic transducers, or the ultrasound sensor 20 may include capacitive micromachined ultrasound transducers (CMUT) in which the energy transduction is provided due to a change in capacitance.

The ultrasound sensor 20 may further include an ultrasound focusing lens, which may be positioned over the transducer array, and which may form a part of the sensing surface. The focusing lens may be any lens operable to focus a transmitted ultrasound beam from the transducer array toward a patient and/or to focus a reflected ultrasound beam from the patient to the transducer array. The ultrasound focusing lens may have a curved surface shape in some embodiments. The ultrasound focusing lens may have different shapes, depending on a desired application, e.g., a desired operating frequency, or the like. The ultrasound focusing lens may be formed of any suitable material, and in some embodiments, the ultrasound focusing lens is formed of a room-temperature-vulcanizing (RTV) rubber material.

In some embodiments, first and second membranes are positioned adjacent to opposite sides of the ultrasound sensor 20 and form a part of the sensing surface. The membranes may be formed of any suitable material, and in some embodiments, the membranes are formed of a room-temperature-vulcanizing (RTV) rubber material. In some embodiments, the membranes are formed of a same material as the ultrasound focusing lens.

Figure 2:
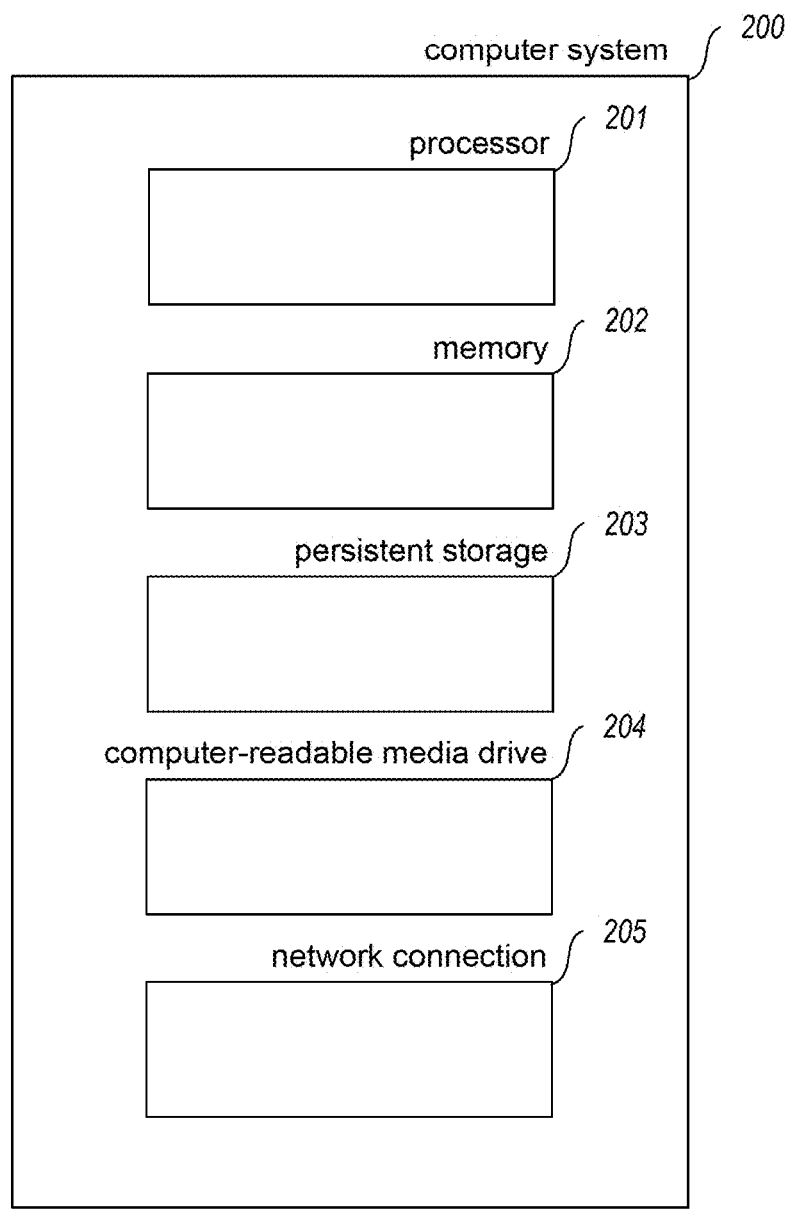
FIG. 2 is a block diagram showing some of the components typically incorporated in at least some of the computer systems and other devices on which the facility operates.

FIG. 2 is a block diagram showing some of the components typically incorporated in at least some of the computer systems and other devices on which the facility operates. In various embodiments, these computer systems and other devices 200 can include server computer systems, cloud computing platforms or virtual machines in other configurations, desktop computer systems, laptop computer systems, netbooks, mobile phones, personal digital assistants, televisions, cameras, automobile computers, electronic media players, physiological sensing devices, and/or their associated display devices, etc. In various embodiments, the computer systems and devices include zero or more of each of the following: a processor 201 for executing computer programs and/or training or applying machine learning models, such as a CPU, GPU, TPU, NNP, FPGA, or ASIC; a computer memory 202 for storing programs and data while they are being used, including the facility and associated data, an operating system including a kernel, and device drivers; a persistent storage device 203, such as a hard drive or flash drive for persistently storing programs and data; a computer-readable media drive 204, such as a floppy, CD-ROM, or DVD drive, for reading programs and data stored on a computer-readable medium; and a network connection 205 for connecting the computer system to other computer systems to send and/or receive data, such as via the Internet or another network and its networking hardware, such as switches, routers, repeaters, electrical cables and optical fibers, light emitters and receivers, radio transmitters and receivers, and the like. While computer systems configured as described above are typically used to support the operation of the facility, those skilled in the art will appreciate that the facility may be implemented using devices of various types and configurations, and having various components.

Figure 3:
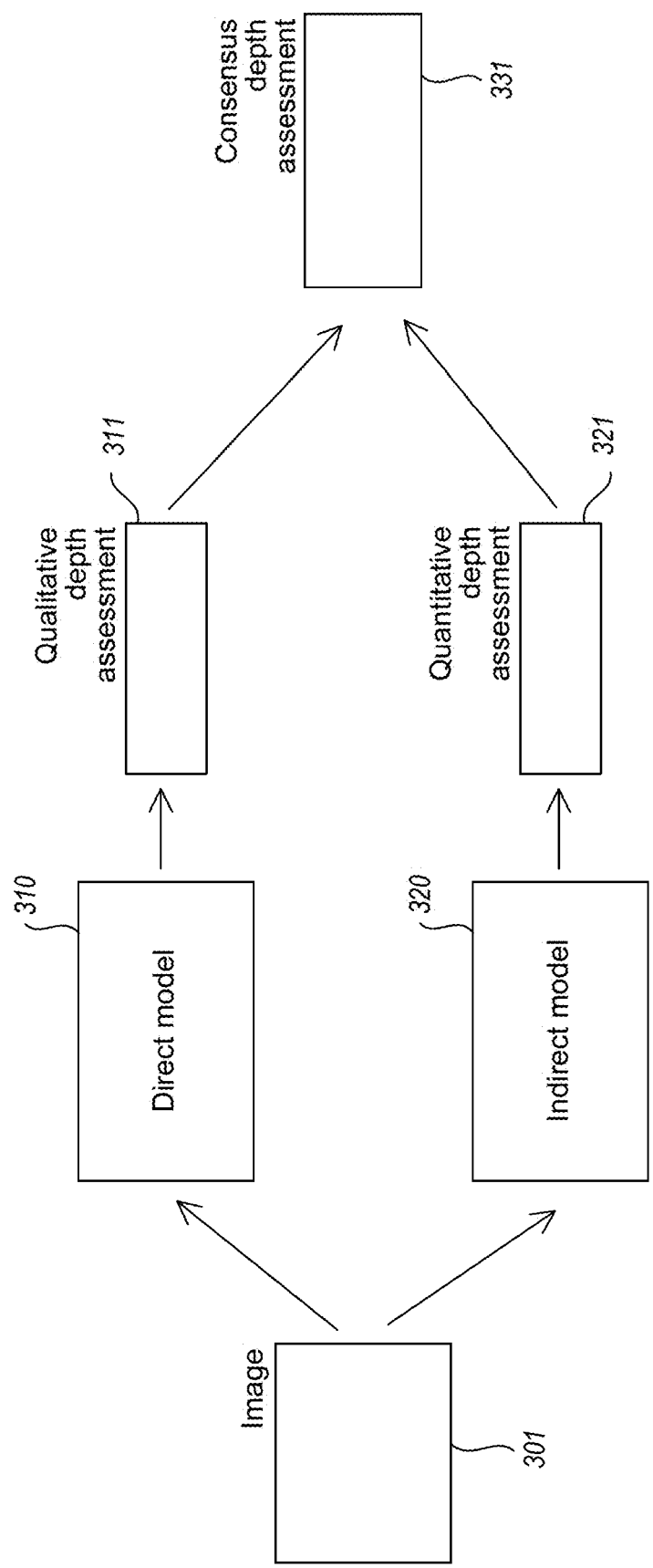
FIG. 3 is a data flow diagram providing an overview of the operation of the facility.

FIG. 3 is a data flow diagram providing an overview of the operation of the facility. The facility passes an ultrasound image 301 to each of a direct machine learning model 310 and an indirect machine learning model 320. The direct model analyzes the ultrasound image to produce a qualitative depth assessment 311. The indirect model analyzes the image to produce a quantitative depth assessment 321. From the qualitative and quantitative depth assessments, the facility generates a consensus depth assessment 331, which in some embodiments it uses as a basis for determining whether to cause the capture of an additional ultrasound image with a particular directed distance change in depth.

Figure 4:
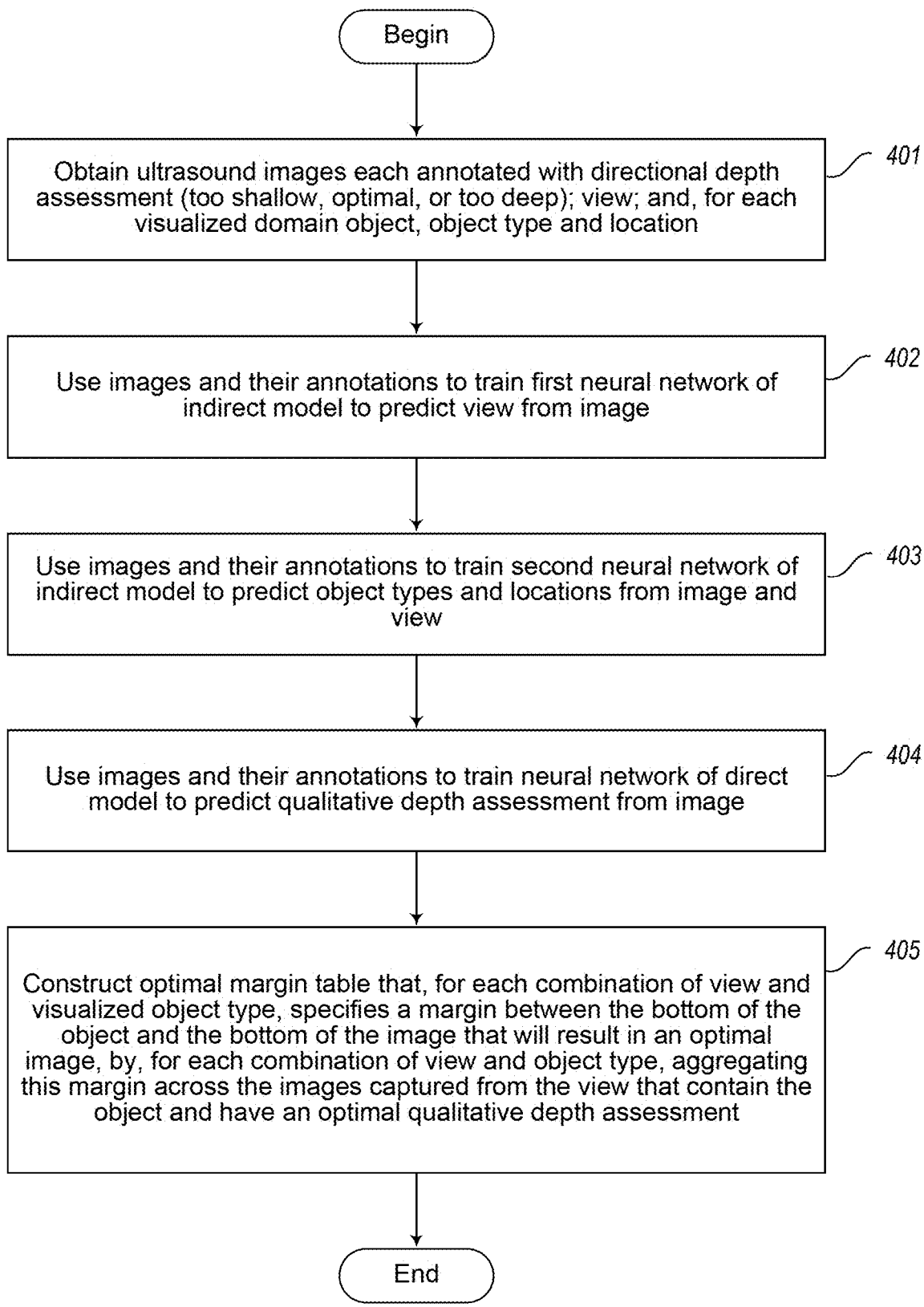
FIG. 4 is a flow diagram showing a process performed by the facility in some embodiments to construct and train the direct and indirect models.

FIG. 4 is a flow diagram showing a process performed by the facility in some embodiments to construct and train the direct and indirect models. In act 401, the facility obtains training ultrasound images each annotated with (1) a directional depth assessment for the ultrasound image; (2) a view from which the ultrasound image was captured; and (3) for each visualized domain object, the type and location of the object. In some embodiments, the directional depth assessment specifies either that the depth is too shallow (i.e., too small), optimal, or too deep (i.e., too large).

In act 402, the facility uses the training images and their annotations obtained in act 401 to train a first neural network of the indirect model to predict the view that each training image was captured from based upon the training image. In act 403, the facility uses the training images and their annotations obtained in act 401 to train a second neural network of the indirect model to predict the types and locations of anatomical structures ("objects") visualized in each training image, based on the training image and the view. In act 404, the facility uses the training images and their annotations obtained in act 401 to train a neural network of the direct model to predict each training image's qualitative depth assessment from the training image.

In act 405, the facility constructs an optimal margin table that, for each combination of view and visualized object type, specifies the margin between the bottom of the object and the bottom of the image that will result in an optimal image ("optimal margin"). The facility determines this optimal margin by, for each combination of view and object type, aggregating across the training images captured from that view that contain one or more objects of that type and that have an optimal qualitative depth assessment the margin between the bottom of these objects and the bottom of the image. After act 405, this process concludes.

Those skilled in the art will appreciate that the acts shown in FIG. 4 and in each of the flow diagrams discussed below may be altered in a variety of ways. For example, the order of the acts may be rearranged; some acts may be performed in parallel; shown acts may be omitted, or other acts may be included; a shown act may be divided into subacts, or multiple shown acts may be combined into a single act, etc.

Figure 5:
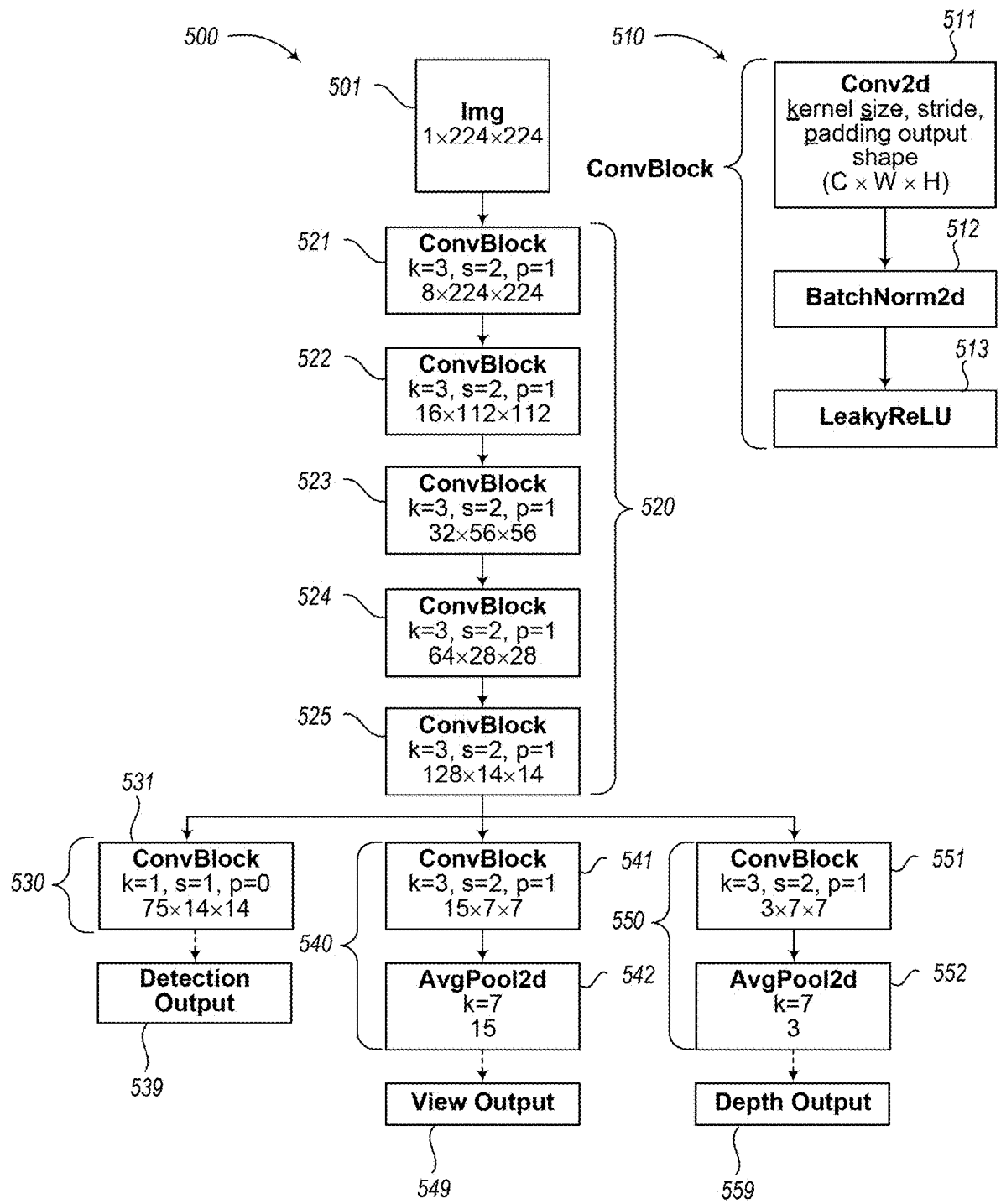
FIG. 5 is a neural network architecture diagram showing architectural details of neural networks trained and/or applied by the facility in some embodiments.

FIG. 5 is a neural network architecture diagram showing architectural details of neural networks trained and/or applied by the facility in some embodiments. As shown, the three neural networks used by the facility are connected in a single convolutional neural network ("CNN") 500. The CNN is composed of a series of convolutional blocks ("ConvBlocks") 510 that each consist of a 2D Convolutional layer 511, followed by a 2D Batch normalization layer 512 and a Leaky ReLU activation function layer 513. In addition to convolutional blocks 521-525, 531, 541, and 551, the CNN includes 2D Average Pooling layers 542 and 552.

The CNN takes as its input an ultrasound image 501, such as a 1×224×224 grayscale ultrasound image. The CNN produces three outputs: a detection output 539 that predicts the locations and dimensions of structures of interest in the ultrasound image (e.g., Left Ventricle); a view output 549 that predicts the standard ultrasound view ("view," or "window") in which the ultrasound image was captured (e.g., Apical 4-Chamber); and a depth output 559 that predicts whether the depth setting is too deep, too shallow, or optimal. In some embodiments, the detection output is expressed in You Only Look Once ("YOLO") format, described by Joseph Redmon and Ali Farhadi, YOLOv3: An Incremental Improvement, University of Washington, 2018, available at arxiv.org/abs/1804.02767, which is hereby incorporated by reference in its entirety. In cases where a document incorporated herein by reference conflicts with the present disclosure, the present disclosure controls.

The neural network referred to above as the neural network of the direct model is made up of branch 520—shared with the other two constituent neural networks—and branch 550, and produces depth output 559. The neural network referred to above as the first neural network of the indirect model is made up of branches 520 and 540, and produces view output 549. The neural network referred to above as the second neural network of the indirect model is made up of branches 520 and 530, and produces detection output 539.

FIG. 6 is a table diagram showing sample contents of an optimal margin table constructed and/or used by the facility in some embodiments. The table 600 is made up of rows such as rows 601-609, each corresponding to a different combination of view and object type. Each row is divided into the following columns: a view column 611 identifying a standard view from which ultrasound images are captured; an object name column 612 identifying an object type whose objects can occur in the view stored in the view column; and an average optimal margin column 613 that, for the combination of view and object type identified by the view and object name columns, specifies an optimal distance from the bottom of objects of the identified object type to the bottom of an ultrasound image captured from the identified view. In some embodiments, as described above, the facility determines these values by aggregating—such as averaging—this margin distance for objects of this type in training images captured from this view that have been tagged as being at an optimal depth.

While FIG. 6 shows a table whose contents and organization are designed to make them more comprehensible by a human reader, those skilled in the art will appreciate that actual data structures used by the facility to store this information may differ from the table shown, in that they, for example, may be organized in a different manner; may contain more or less information than shown; may be compressed, encrypted, and/or indexed; may contain a much larger number of rows than shown, etc.

Figure 7:
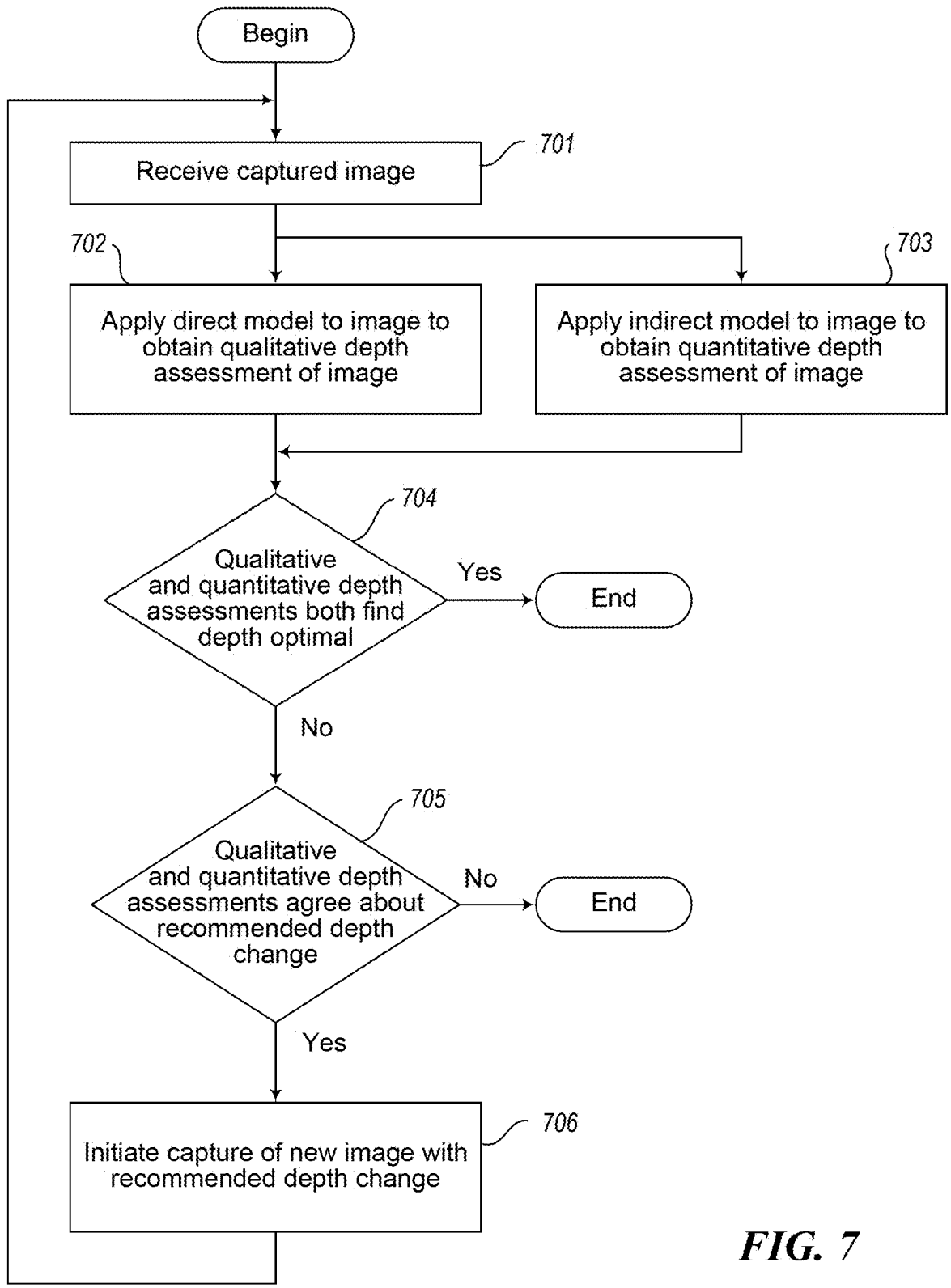
FIG. 7 is a flow diagram showing a process performed by the facility in some embodiments to adjust the depth of an ultrasound image to be more optimal.

FIG. 7 is a flow diagram showing a process performed by the facility in some embodiments to adjust the depth of an ultrasound image to be more optimal. In act 701, the facility receives a captured ultrasound image. After act 701, the facility performs both act 702 and act 703. In act 702, the facility applies the direct model to the image received in act 701 to obtain a qualitative depth assessment of the ultrasound image. Act 702 is discussed in greater detail below in connection with FIG. 8. In act 703, the facility applies the indirect model to the image received in act 701 to obtain a quantitative depth assessment of the image. Act 703 is discussed in greater detail below in connection with FIG. 9. After acts 702 and 703, the facility continues in act 704. In act 704, if the qualitative depth assessment obtained in act 702 and the quantitative depth assessment obtained in act 703 both find the depth to be optimal, then this process concludes, else the facility continues in act 705. In act 705, if the qualitative and quantitative depth assessment agree about the recommended direction in which to change the depth, then the facility continues in act 706, else this process concludes. In act 706, the facility initiates the capture of a new image with the depth change recommended by the indirect model in the quantitative depth assessment. After act 706, the facility continues in act 701 to receive and process the next captured image.

Figure 8:
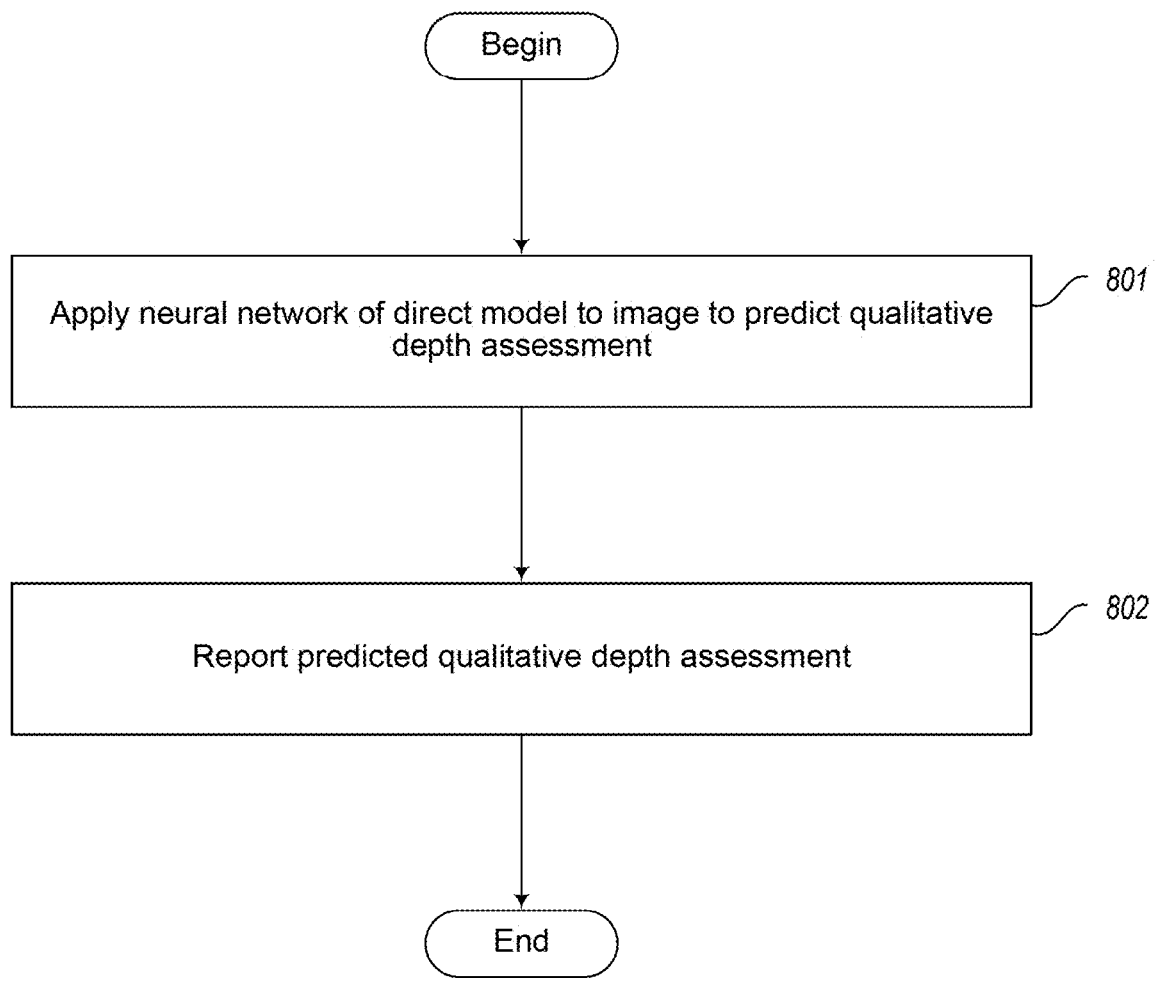
FIG. 8 is a flow diagram showing a process performed by the facility in some embodiments to apply the direct model to an ultrasound image.

FIG. 8 is a flow diagram showing a process performed by the facility in some embodiments to apply the direct model to an ultrasound image, such as in act 702 shown in FIG. 7. In act 801, the facility applies the neural network of the direct model to the ultrasound image to predict a qualitative depth assessment. In act 802, the facility reports the qualitative depth assessment predicted in act 801. After act 802, this process concludes.

Figure 9:
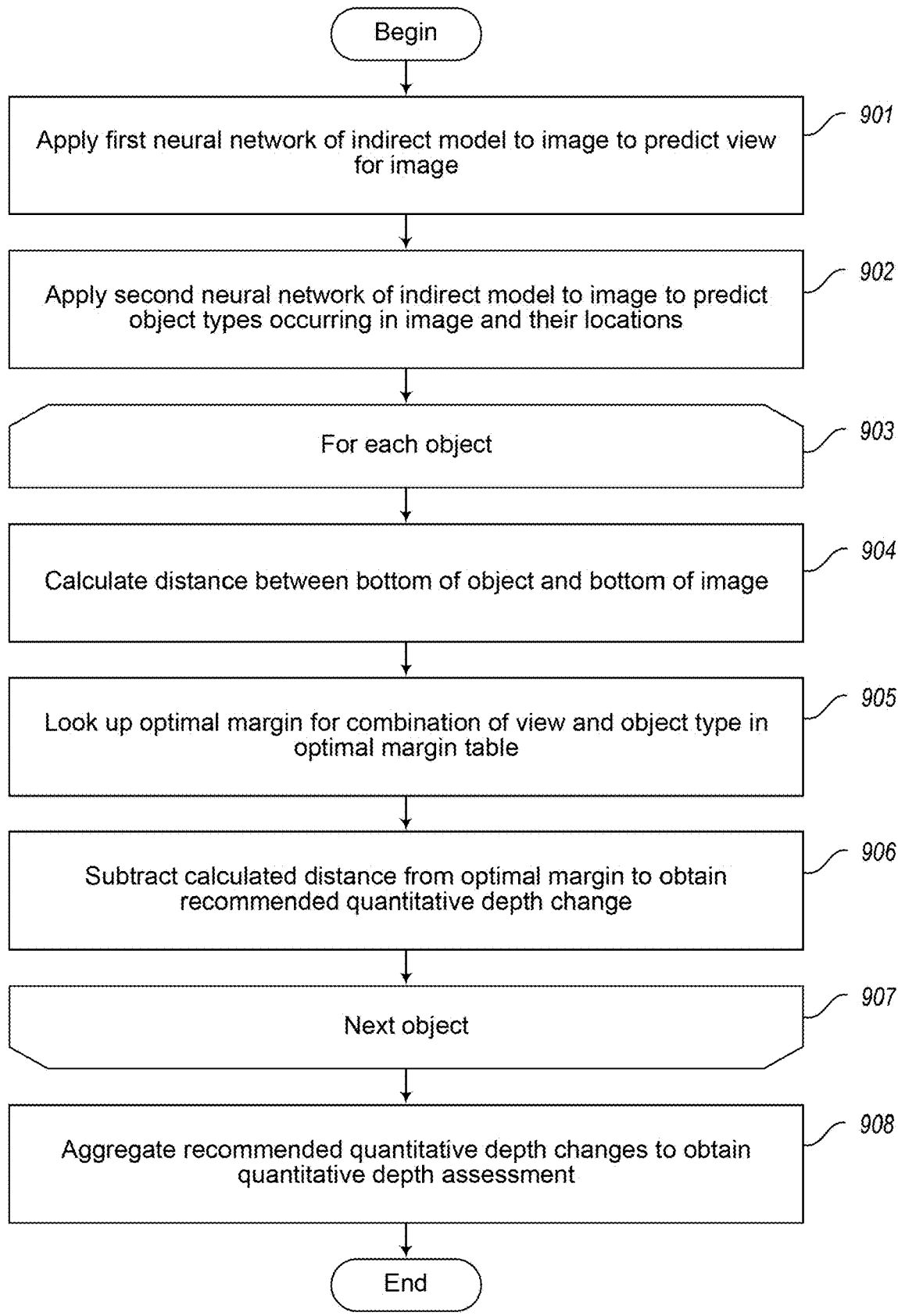
FIG. 9 is a flow diagram showing a process performed by the facility in some embodiments to apply the indirect model to an ultrasound image.

FIG. 9 is a flow diagram showing a process performed by the facility in some embodiments to apply the indirect model to an ultrasound image, such as in act 703 shown in FIG. 7. In act 901, the facility applies the first neural network of the indirect model to the image to predict the view from which the image was captured. In act 902, the facility applies the second neural network of the indirect model to the image to predict object types occurring in the image and their locations. In acts 903-907, the facility loops through each object predicted to occur in the ultrasound image in act 902. In act 904, the facility calculates the distance between the bottom of the object and the bottom of the ultrasound image. In act 905, the facility looks up in the optimal margin table the optimal margin for the combination of the view predicted in act 901 and the object type predicted in act 902. In act 906, the facility subtracts the distance calculated in act 904 from the optimal margin looked up in act 905 to obtain a recommended quantitative depth change. In act 907, if additional objects remain to be processed, then the facility continues in act 903 to process the next object, else the facility continues in act 908. In act 908, the facility aggregates the recommended quantitative depth changes obtained in act 906— such as by averaging them—to obtain a quantitative depth assessment. After act 908, this process concludes.

Figure 10:
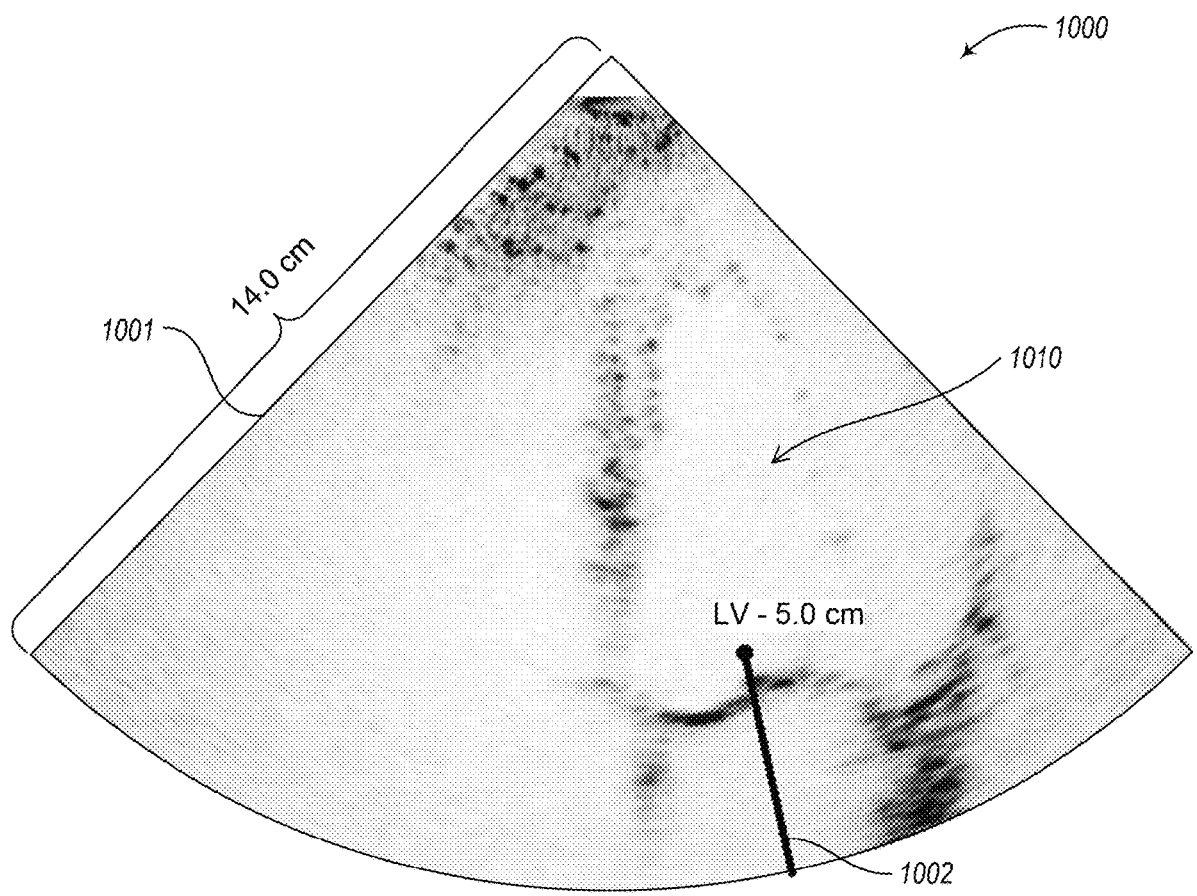
FIG. 10 is an ultrasound diagram showing an ultrasound image captured from the Apical 4-chamber view in which the facility determines the depth is too small.
Figure 11:
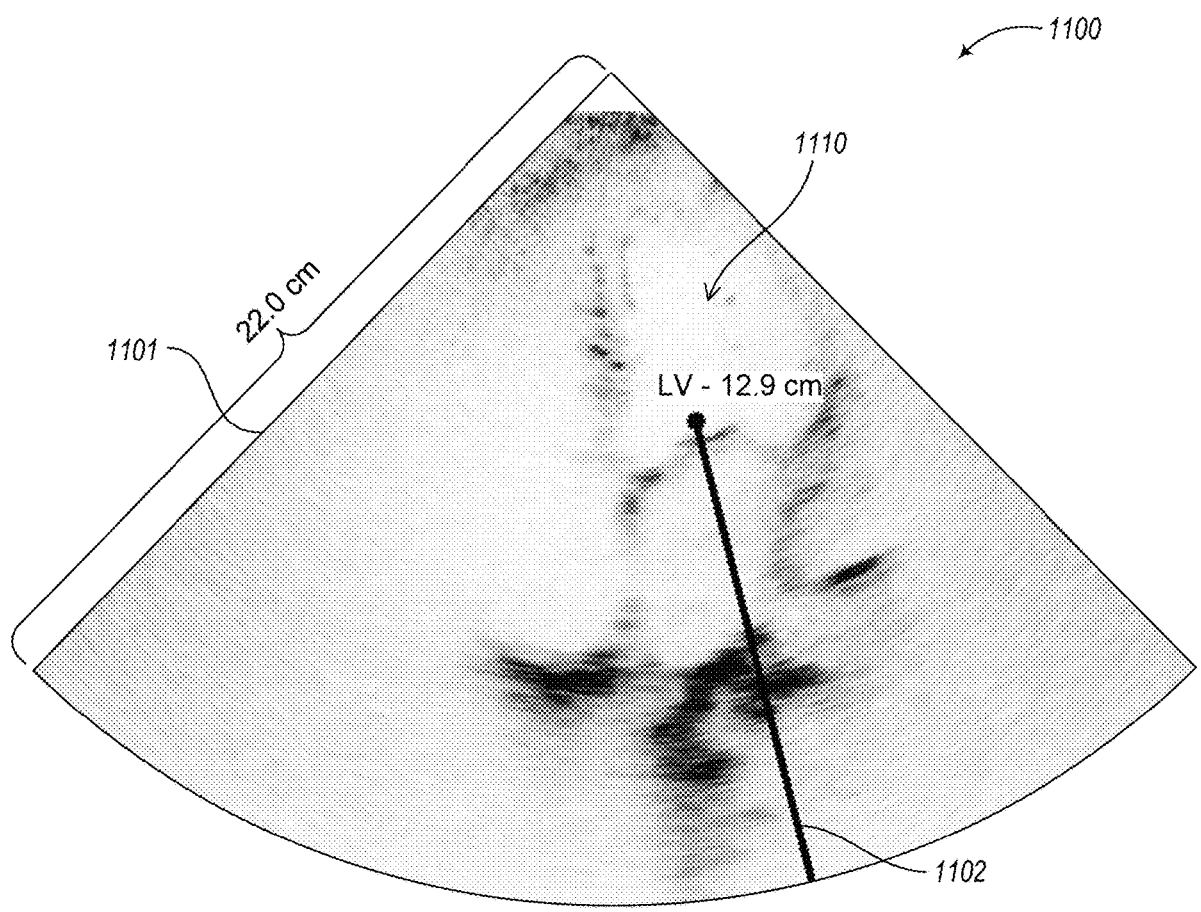
FIG. 11 is an ultrasound diagram showing an ultrasound image captured from the Apical 4-chamber view in which the facility determines the depth is too large.
Figure 12:
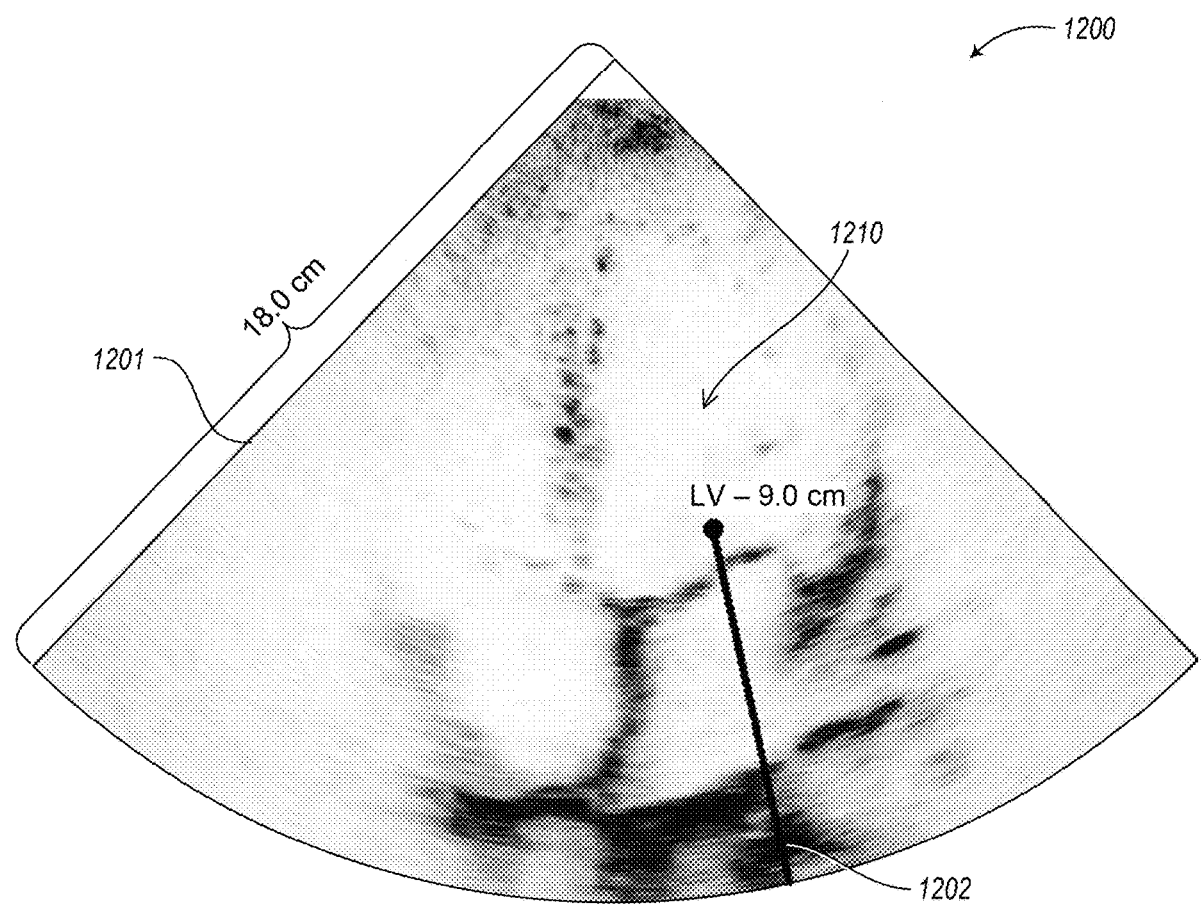
FIG. 12 is an ultrasound diagram showing an ultrasound image captured from the Apical 4-chamber view in which the facility determines the depth is within tolerance of optimal.

FIGS. 10-12 are ultrasound diagrams showing ultrasound images captured from the same patient and the same view—the Apical 4-chamber view of the heart. These figures respectively show images captured where the depth setting is too shallow, too deep, and optimal. In these figures, the ultrasound images are black/white-inverted from their typical form to maximize intelligibility and reproducibility.

FIG. 10 is an ultrasound diagram showing an ultrasound image captured from the Apical 4-chamber view in which the facility determines the depth is too small. In the diagram 1000, it can be seen that the image has a depth 1001 of 13.0 cm, and that the bottom of the left ventricle 1010 is a distance 1002 of 5.0 cm from the bottom of the image, i.e., the curved base of the ultrasound cone shown nearest the bottom of the diagram. In some embodiments, the facility's direct model finds this depth to be too small, and the facility's indirect model compares this margin of 5.0 cm to the optimal margin of 8.88 cm specified in row 605 of the optimal margin table shown in FIG. 6, and finds the margin and therefore depth of the image to be 3.88 cm too small. Accordingly, the facility captures an additional image at a larger depth, such as a depth 3.88 cm larger.

FIG. 11 is an ultrasound diagram showing an ultrasound image captured from the Apical 4-chamber view in which the facility determines the depth is too large. In the diagram 1100, it can be seen that the image has a depth 1101 of 22.0 cm, and that the bottom of the left ventricle 1110 is a distance 1102 of 12.9 cm from the bottom of the image. In some embodiments, the facility's direct model finds this depth to be too large, and the facility's indirect model compares this margin of 12.9 cm to the optimal margin of 8.88 cm specified in row 605 of the optimal margin table shown in FIG. 6, and finds the margin and therefore depth of the image to be 4.01 cm too large. Accordingly, the ability captures an additional image at a smaller depth, such as a depth 4.01 cm smaller.

FIG. 12 is an ultrasound diagram showing an ultrasound image captured from the Apical 4-chamber view in which the facility determines the depth is within tolerance of optimal. In the diagram 1200, it can be seen that the image has a depth 1201 of 18.0 cm, and that the bottom of the left ventricle 1210 is a distance 1202 of 9.0 cm from the bottom of the image. In some embodiments, the facility's direct model finds this depth to be optimal, and the facility's indirect model compares this margin of 9.0 cm to the optimal margin of 8.88 cm specified in row 605 of the optimal margin table shown in FIG. 6, and finds the margin of the image to be within tolerance of optimal, at 0.12 cm away. Accordingly, the facility does not capture any additional images.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet, are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A system, comprising:
  an ultrasound sensing device having a depth configuration setting; and
  a computing device, the computing device comprising:
    a communication interface configured to directly receive ultrasound echo data sensed by the ultrasound sensing device from a person, the received ultrasound echo data comprising a sequence of one or more ultrasound images each captured by the ultrasound sensing device using a particular depth configuration setting value;
    a memory configured to:
      store a machine learning model for producing results each in response to an ultrasound image in the sequence, the machine learning model including one or more convolutional blocks, wherein each convolutional block is configured to perform at least one aspect of determining whether depth configuration settings of an ultrasound device that obtained data to generate the ultrasound image are within tolerance of optimal, too large, or too small;
    a processor configured to:
      for each ultrasound image of the sequence, in response to its receipt by the communications interface:
        subject the ultrasound image to the machine learning model to produce a result, the result indicating whether the ultrasound image is more consistent with similar training images annotated as having been captured using depth configuration setting values that are:
          within tolerance of optimal,
          too large, or
          too small;
        where the result indicates that the ultrasound image is more consistent with similar training images annotated as having been captured using depth configuration setting values that are within tolerance of optimal than with training images annotated as having been captured using depth configuration setting values that are too large or training images annotated as having been captured using depth configuration setting values that are too small, automatically cause capture of the sequence of ultrasound images to be ended;

where the result indicates that the ultrasound image is more consistent with similar training images annotated as having been captured using depth configuration setting values that are too large than with training images annotated as having been captured using depth configuration setting values that are within tolerance of optimal or training images annotated as having been captured using depth configuration setting values that are too small, automatically cause the next ultrasound image of the sequence to be captured using a depth configuration setting value that is smaller than the depth configuration setting value used to capture the ultrasound image; and where the result indicates that the ultrasound image is more consistent with similar training images annotated as having been captured using depth configuration setting values that are too small than with training images annotated as having been captured using depth configuration setting values that are within tolerance of optimal or training images annotated as having been captured using depth configuration setting values that are too large, automatically cause the next ultrasound image of the sequence to be captured using a depth configuration setting value that is larger than the depth configuration setting value used to capture the ultrasound image.

2. The system of claim 1 wherein the ultrasound sensing device comprises a transducer.

3. The system of claim 1 wherein the stored machine learning model has been trained using ultrasound images of hearts, and wherein the ultrasound images of the sequence are ultrasound images of hearts.

4. The system of claim 1 wherein the stored machine learning model is a neural network trained using labeled training ultrasound images to predict the result from the ultrasound image.

5. The system of claim 1 wherein each result further indicates a magnitude by which the depth configuration setting value should be changed in the indicated direction in order to be optimal.

6. The system of claim 5 wherein the stored machine learning model comprises:

a first neural network trained to predict from the ultrasound image a view from which the ultrasound image was captured;

a second neural network trained to predict from the ultrasound image a type and location of one or more objects visualized in the ultrasound image; and a mapping from different combinations of view and object type to an empirically-derived target distance from the location of an object of the object type visualized in an ultrasound image captured from the view to the a bottom end of the ultrasound image representing the greatest depth within the ultrasound image, and wherein subjecting the ultrasound image to the machine learning model comprises, for each of at least one of the visualized objects:

determining the target distance that the mapping maps to from the view predicted by the first neural network and the type predicted for the visualized object by the second neural network;

determining a distance between the visualized object's predicted location and the bottom end of the ultrasound image; and calculating a difference between the target distance and the determined distance.

7. The system of claim 6 wherein subjecting the ultrasound image to the machine learning model further comprises:

across the visualized objects, aggregating the calculated differences.

8. The system of claim 6 wherein the stored machine learning model comprises:

a first submodel that predicts from an ultrasound image whether the ultrasound image was captured at a target depth, and, if not, a direction in which the depth configuration setting value should be adjusted to be closer to target depth; and a second submodel that predicts from an ultrasound image a direction and distance by which the depth configuration setting value should be adjusted to be closer to target depth, and wherein the processor is further configured to:

where the directions predicted by the first and second models are different, automatically ending capture of the sequence of ultrasound images; and where the directions predicted by the first and second models are the same, automatically causing the next ultrasound image of the sequence to be captured using a depth configuration setting value that is the indicated distance in the indicated direction from the depth configuration setting value used to capture the ultrasound image.

9. One or more memories collectively containing a target margin table data structure, the data structure comprising:

a plurality of entries, each entry comprising:

first information identifying an ultrasound view;

second information identifying an anatomical structure among anatomical structures typically visualizable in the ultrasound view identified by the first information; and third information specifying a target margin size that reflects, for ultrasound images captured from the ultrasound view identified by the first information, a target distance from the bottom of visualized instances of the anatomical structure identified by the second information representing the point in the visualized instances of the anatomical structure having the greatest depth to a bottom end of an ultrasound image representing the greatest depth within the ultrasound image, such that, for a particular combination of ultrasound view and anatomical structure, an entry can be selected and its third information retrieved to determine target margin size for that combination of ultrasound view and anatomical structure, and the target margin table data structure is usable to train a neural network for predicting from an ultrasound image whether it was (a) captured at a target depth, (b) captured at a depth less than the target depth, or (c) captured at a depth greater than the target depth.

10. The one or more memories of claim 9 wherein, for each entry, the target margin size specified by the entry's third information is empirically determined by aggregating margins measured in ultrasound images captured from the ultrasound view identified by the entry's first information containing one or more of the anatomical structures identified by the entry's second information that are categorized as optimal by a human domain expert.

11. The one or more memories of claim 9 further containing the trained neural network, the trained neural network including one or more convolutional blocks, wherein each convolutional block is configured to perform at least one aspect of predicting whether an ultrasound image was captured from a target depth, captured at a depth less than target, or captured at a depth greater than the target depth.

12. The one or more memories of claim 9 further containing:
- a first trained neural network for predicting from an ultrasound image an ultrasound view from which it was captured; and
- a second trained neural network for predicting from an ultrasound image, for each of one or more anatomical structures visualized in the ultrasound image, a type and location of the anatomical object, such that the view predicted by the first trained neural network and the type of each visualized anatomical structure predicted by the second trained neural network can be used to select an entry of the target margin table and retrieve the optimal margin specified by the entry's third information, and such that the location of each visualized anatomical structure predicted by the second trained neural network can be used to calculate actual margin for the ultrasound image, and such that the calculated actual margin can be compared to the retrieved target margin.

13. One or more instances of computer-readable media collectively having contents configured to cause a computing system to perform a method, the method comprising:
- receiving an ultrasound image captured from a patient with a particular depth setting;
- subjecting the received ultrasound image to at least one neural network to produce, for each neural network, a result, the neural network including one or more convolutional blocks, wherein each convolutional block is configured to perform at least one aspect of producing results that are used to determine whether depth settings at which an ultrasound image was captured produced a satisfactory result or did not produce a satisfactory result;
- on the basis of the produced results, determining whether the depth setting at which the ultrasound image was captured produced a satisfactory result; and
- in response to determining that the depth setting at which the ultrasound image was captured did not produce a satisfactory result, automatically causing the capture of an additional ultrasound image to be captured from the patient at a depth setting that is different from the depth setting at which the ultrasound image was captured.

14. The one or more instances of computer-readable media of claim 13, the method further comprising:
- on the basis of the produced results, determining a direction in which a target depth setting differs from the depth setting at which the ultrasound image was captured, and wherein the causing causes the additional ultrasound image to be captured from the patient at a depth setting that is different from the depth setting at which the ultrasound image was captured in the determined direction.

15. The one or more instances of computer-readable media of claim 14, the method further comprising:
- on the basis of the produced results, determining a magnitude by which the target depth setting differs from the depth setting at which the ultrasound image was captured, and wherein the causing causes the additional ultrasound image to be captured from the patient at a depth setting that is different from the depth setting at which the ultrasound image was captured by the determined magnitude.

16. The one or more instances of computer-readable media of claim 13, the method further comprising:
- using ultrasound images captured from patients to train the at least one neural network.

* * * * *